United States Patent [19]
Zamenhof

[11] Patent Number: 5,341,292
[45] Date of Patent: Aug. 23, 1994

[54] MONTE CARLO BASED TREATMENT PLANNING FOR NEUTRON CAPTURE THERAPY

[75] Inventor: Robert G. Zamenhof, Brookline, Mass.

[73] Assignee: New England Medical Center Hospitals, Inc., Boston, Mass.

[21] Appl. No.: 893,650

[22] Filed: Jun. 4, 1992

[51] Int. Cl.[5] ............................................. G06F 15/42
[52] U.S. Cl. ............................ 364/413.13; 364/413.26
[58] Field of Search ...................... 364/413.26, 413.22, 364/413.19, 413.14, 413.13; 128/653.1; 600/4

[56] References Cited

U.S. PATENT DOCUMENTS

| | | |
|---|---|---|
| 3,987,281 | 10/1976 | Hodes . |
| 4,869,247 | 9/1989 | Howard et al. . |
| 5,027,818 | 7/1991 | Bova et al. ..................... 364/413.14 |
| 5,117,829 | 6/1992 | Miller et al. ...................... 128/653.1 |
| 5,205,289 | 4/1993 | Hardy et al. .................... 364/413.26 |
| 5,227,969 | 7/1993 | Waggener et al. .............. 364/413.26 |

OTHER PUBLICATIONS

Zamenhof, R. G. et al., "Monte Carlo Treatment Planning and High-Resolution Alpha-Track Autoradiography for Neutron Capture Therapy", Strahlenther. Onkol., 165 (1989), 188–192.

Zamenhof, R. G. et al., "Monte Carlo Based Dosimetry and Treatment Planning for Neutron Capture Therapy of Brain Tumors", Neutron Beam Design, Development, and Performance for Neutron Capture Therapy, 1990, 283–305.

Zamenhof, R. G. et al., "Treatment Planning for Neutron Capture Therapy of Glioblastoma Multiforme Using . . .", Progress in Neutron Capture Therapy for Cancer, pp. 173–177 no date known.

Weissberger, M. A. et al., "Computed Tomography Scanning for the Measurement of Bone Mineral in the Human Spine", Journal of Computer Assisted Tomography, 2:253–262, Jul. 1978.

Zamenhof, R. G. et al., "Boron Neutron Capture Therapy for the Treatment of Cerebral Gliomas. I: Theoretical Evaluation of the Efficacy of Various Neutron Beams", Medical Physics, vol. 2, No. 2, Mar./Apr. 1975, 47–60.

Primary Examiner—Robert A. Weinhardt
Attorney, Agent, or Firm—Fish & Richardson

[57] ABSTRACT

A method for developing a treatment plan for neutron capture therapy of a target organ including the steps of using a diagnostic cross-sectional scanner to scan the target organ to generate cross-sectional images of the organ; generating a three-dimensional model of the organ from the cross-sectional images, the model including information about internal features of the organ; and using the three-dimensional model to compute expected radiation doses throughout the organ assuming a given arrangement of one or more neutron beams.

19 Claims, 4 Drawing Sheets

MONTE CARLO BASED TREATMENT PLANNING FOR NEUTRON CAPTURE THERAPY

BACKGROUND OF THE INVENTION

The invention relates to treatment planning for neutron capture therapy.

Neutron Capture Therapy (NCT) was "born" in 1936, soon after the 1932 discovery of the neutron by Chadwick. Gordon Locher, a biophysicist at Strathmore College, proposed the principle of boron-neutron capture therapy as a potential future method of treating cancer. Boron-10, a naturally occurring isotope of boron, had been known since the 1934 work of Goldhaber in Cambridge, England to have an unusually high avidity for capturing slow ("thermal") neutrons. Immediately after capturing a slow neutron, $^{10}B$ was found to disintegrate into an energetic alpha particle and a recoiling $^{7}Li$ ion, with a combined range in water of about 12–13 microns. Locher proposed, with impressive foresight, that if boron could be selectively concentrated in a patient's tumor and the area then flooded with slow neutrons, a higher radiation dose to tumor would result, thereby killing the tumor.

In 1940, Kruger at the University of Illinois reported on the reduced viability of transplanted mouse tumors following their exposure to boric acid paste and irradiation with slow neutrons. Zahl also reported the regression of mouse sarcomas in vivo after their infiltration with boric acid paste.

It was realized, even in those early years, that because of the poor penetration of slow neutrons in tissue NCT would be difficult to apply to the treatment of deeply-seated tumors in humans. In 1941, Zahl suggested that to overcome this potential problem, neutrons of higher energy would need to be used; these "epithermal" neutrons would not be captured by $^{10}B$ until they had slowed down to thermal energies at a few centimeters depth in tissue. Today, the only two available clinical neutron beams designed for NCT are at MIT and BNL and are, indeed, epithermal beams.

In 1950/51 William Sweet, at Massachusetts General Hospital, Boston, and Lee Farr at Brookhaven National Laboratories (BNL), Long Island, N.Y. both proposed initiation of clinical studies of NCT using the newly commissioned Brookhaven Graphite Research Reactor (BGRR). In 1951, a clinical thermal neutron beam became available at the BGRR, and over the following two years ten patients with high-grade brain tumors were treated by NCT by Farr and Sweet. The form of the boron used was $^{10}B$-enriched borax, administered to the patients intravenously shortly prior to neutron irradiation. These patients were highly advanced cases, in most cases already pre-irradiated by conventional radiotherapy, and not selected to exclude deeply-seated tumors. No observable benefit was derived from this first series of NCT patients, neither was there any serious radiation damage to normal tissues. However, because the borax was found to be somewhat toxic, a different boron compound, sodium pentaborate, was used in the next series of nine high-grade brain tumor patients.

An unexpected new problem arose with this second series of BNL patients, probably related to the higher circulating blood concentrations of the sodium pentaborate compound. These patients exhibited quite severe radiation injuries to the scalp and superficial normal brain. In a third series of patients treated by NCT at the BGRR, the pentaborate boron compound was delivered into the internal carotid artery in order to try to minimize the blood boron levels, and the total neutron fluence delivered was reduced. In these patients severe scalp injuries were avoided, but as with the previous patients no significant benefit of the NCT was evident.

During 1959–1961, a third series of seventeen high-grade brain tumor patients was treated by NCT at BNL at the newly commissioned Brookhaven Medical Research Reactor (BMRR). No observable benefit in terms of increased survival accrued to these patients, with the possible exception of one. In this patient, who subsequently died of distance metastases, pathology on the brain showed no viable tumor present, thus suggesting that a local cure might have been achieved. This appears to be the only definitive evidence of successful NCT in humans from the early clinical trials.

During the same 1959–1961 period, William Sweet with the help of a physicist Gordon Brownell treated seventeen high-grade brain tumor patients with the clinical thermal neutron beam at the recently commissioned MIT Research Reactor, MITR-I, using a different boron compound, p-carboxybenzene boronic acid, intravenously administered. This compound was developed by a chemist at the Massachusetts General Hospital, Albert Soloway. Two further patients were treated by NCT using yet another compound developed by Soloway, sodium perhydrodecaborate. This latter compound appeared to be less toxic and contained a higher weight fraction of boron than the earlier compounds. Unlike the upward facing beam of the BGRR or the horizontal beam of the BMRR, the MITR-I beam was downward facing, emerging from the ceiling of a specially constructed treatment room beneath the reactor. This enabled Sweet to surgically reflect the scalp, skull, and dura, and to resect any gross tumor immediately prior to irradiation. The patients were then intraoperatively treated through an open craniotomy. Treatment of the patients in this fashion was facilitated by the orientation of the MITR-I neutron beam. This maneuver theoretically increased the depth to which the therapy could be effective, mimicking in a sense the anticipated effect of the epithermal neutron beam proposed in the 1940's by Kruger. Once again, although scalp injuries were avoided, some normal brain injuries resulted and no discernable benefit in terms of extended lifespan accrued.

Because of the discouraging results of the four patient series at BNL and MIT, clinical NCT in the U.S. was abandoned. Despite these setbacks for NCT, two research groups, at Massachusetts General Hospital/MIT under the direction of William Sweet and Gordon Brownell, and at BNL under the direction of Ralph Fairchild, continued to study NCT from the perspective of developing improved boronated compounds, improved neutron beams (initially improving the quality of the thermal beams, and later developing epithermal beams), and analytic methods for the measurement of boron concentrations in tissues and in blood. Deficits in the following three areas, it is now believed, were primarily responsible for the earlier failures of NCT: the lack of boron compounds exhibiting high tumor/blood partition; the poor tissue penetrability of the existing thermal neutron beams—even with intraoperative treatment; and the lack of "on-line" analytic methods to assay the blood and tissue boron concentrations close to the time of neutron irradiation.

Monte Carlo-based treatment planning techniques for neutron capture therapy have been developed in support of the New England Medical Center/Massachusetts Institute of Technology program in neutron capture therapy (NCT). These techniques enable dose distributions to be displayed as easily understandable isocontours superimposed on precisely corresponding CT or MRI diagnostic images of the animal or human body part being irradiated. This provides the radiation oncologist with a display of the doses received both by the tumor and by various normal tissues. Furthermore, in those patients who do not survive it provides the opportunity to retrospectively perform accurate dosimetric/pathological correlations leading to improved understanding of the clinical response to NCT. The details of this approach are presented and a typical treatment plan involving the parallel-opposed epithermal neutron irradiation of a patient with a glioblastoma multiforme is presented.

Accurate treatment planning for NCT, as for any form of experimental radiation therapy, is beneficial not only for the safety and optimal management of the patient but also for providing correlated radiological/pathological information in those patients who ultimately fail the experimental therapy. This allows the dose-response properties of a new radiation modality to be better understood. Computer-aided treatment planning approaches specifically for NCT of human subjects have previously been reported. See, for example, references 1–4 in the table of references identified as Table A at the end of the specification. (Note that all subsequent references to related articles appear in parentheses and identify the number of the reference in Table A. All of the references listed Table A are incorporated herein by reference.)

SUMMARY OF THE INVENTION

In general, in one aspect, the invention is a method of developing a treatment plan for neutron capture therapy of a target organ. The method includes the steps of using a diagnostic cross-sectional scanner to scan the target organ to generate cross-sectional images of the organ; generating a three-dimensional model of the organ from the cross-sectional images, the model including information about internal features of the organ; and using the three-dimensional model to compute expected radiation doses throughout the organ assuming a given arrangement of one or more neutron beams.

Preferred embodiments include the following features. The diagnostic cross-sectional scanner is a CT scanner. The computing step uses Monte Carlo simulation techniques to compute expected radiation doses. The method also includes the step of identifying on the image of the organ a region within the organ that is believed to contain tumor and the generating step models the identified region as having a higher boron concentration than the part of the head outside the region. The three-dimensional model is a three-dimensional array of three-dimensional cells of uniform dimension and the model generating step assigns each of the cells a corresponding one of a plurality of predetermined materials based upon the CT image value for that cell. The method also includes the steps of selecting a cross-section of the organ for which dose information is desired; computing isocontours for the selected cross-section from the expected radiation doses; and displaying the computed isocontours over a CT image of the selected cross-section. After selecting a cross-section of the organ for which dose information is desired, the method further includes the step of setting the computed dose values outside of the head to zero before computing the isocontours.

Also in preferred embodiments, each of the array of cross-sectional images is an matrix of data elements, and the model generating step includes the steps of assigning one of a plurality of predetermined materials to each of the data elements of the matrices, thereby generating an intermediate model; and constructing the three-dimensional model from the intermediate model. The intermediate model is a three-dimensional array of subcells, the three-dimensional model is an array of cells and each cell is made up of a corresponding plurality of subcells. The model generating step includes the step of computing a given cell a percentage of each of the plurality of the predetermined materials that is assigned to the subcells that correspond to the given cell and assigning to the given cell a composition that corresponds to the computed percentages of the plurality of predetermined materials that are assigned to the subcells that correspond to the given cell. The composition contains quantized amounts of the plurality of predetermined materials. The plurality of predetermined materials includes bone, normal soft tissue, tumor soft tissue, and air. The normal soft tissue and the tumor soft tissue contain different amounts of boron.

An advantage of the invention is that it more accurately models the organ for which an NCT treatment plan is prepared and thus yields a more accurate treatment plan. In addition, the resulting treatment plan accounts for the effect of boron concentration within the organ.

Other advantages and features will become apparent from the following description of the preferred embodiment and from the claims.

DESCRIPTION OF THE PREFERRED EMBODIMENT

Figure 1:
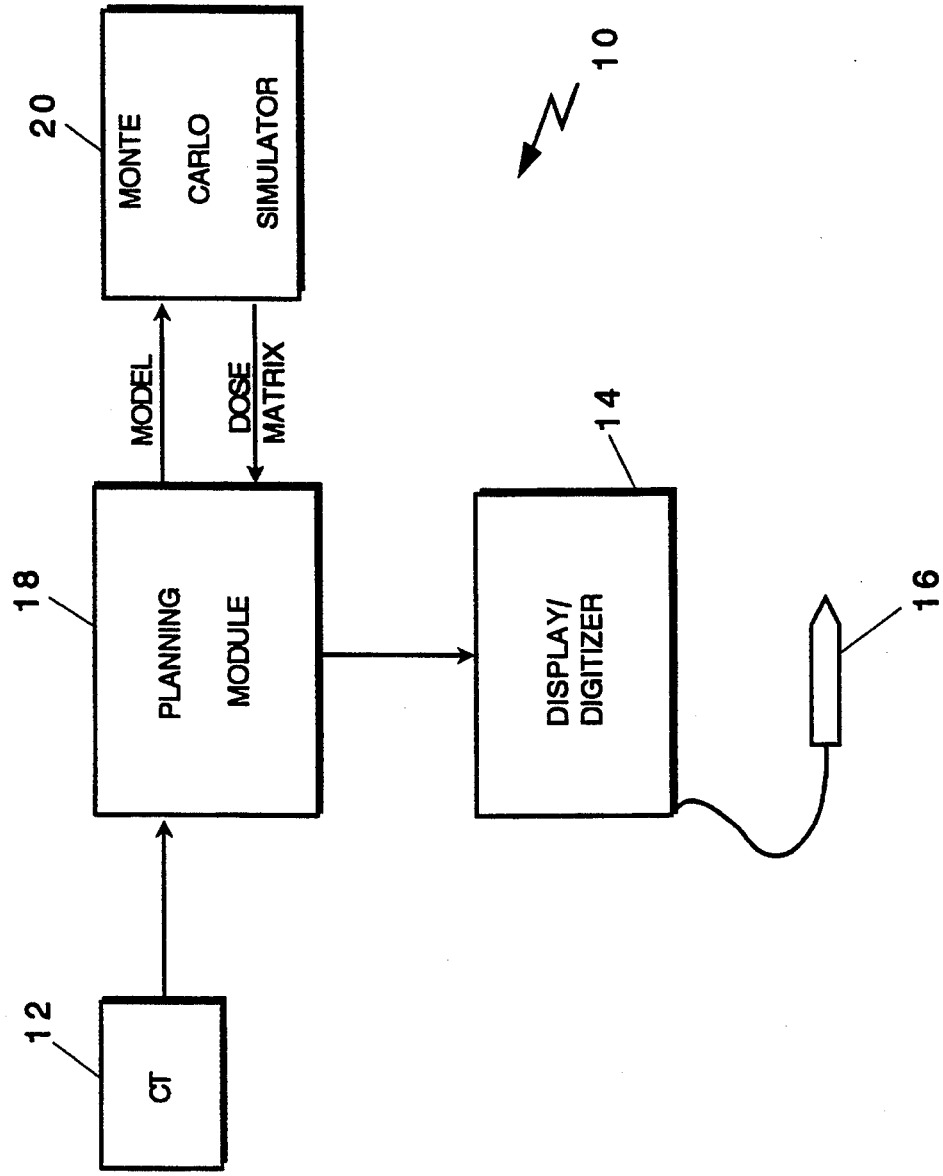
Figure 2A:
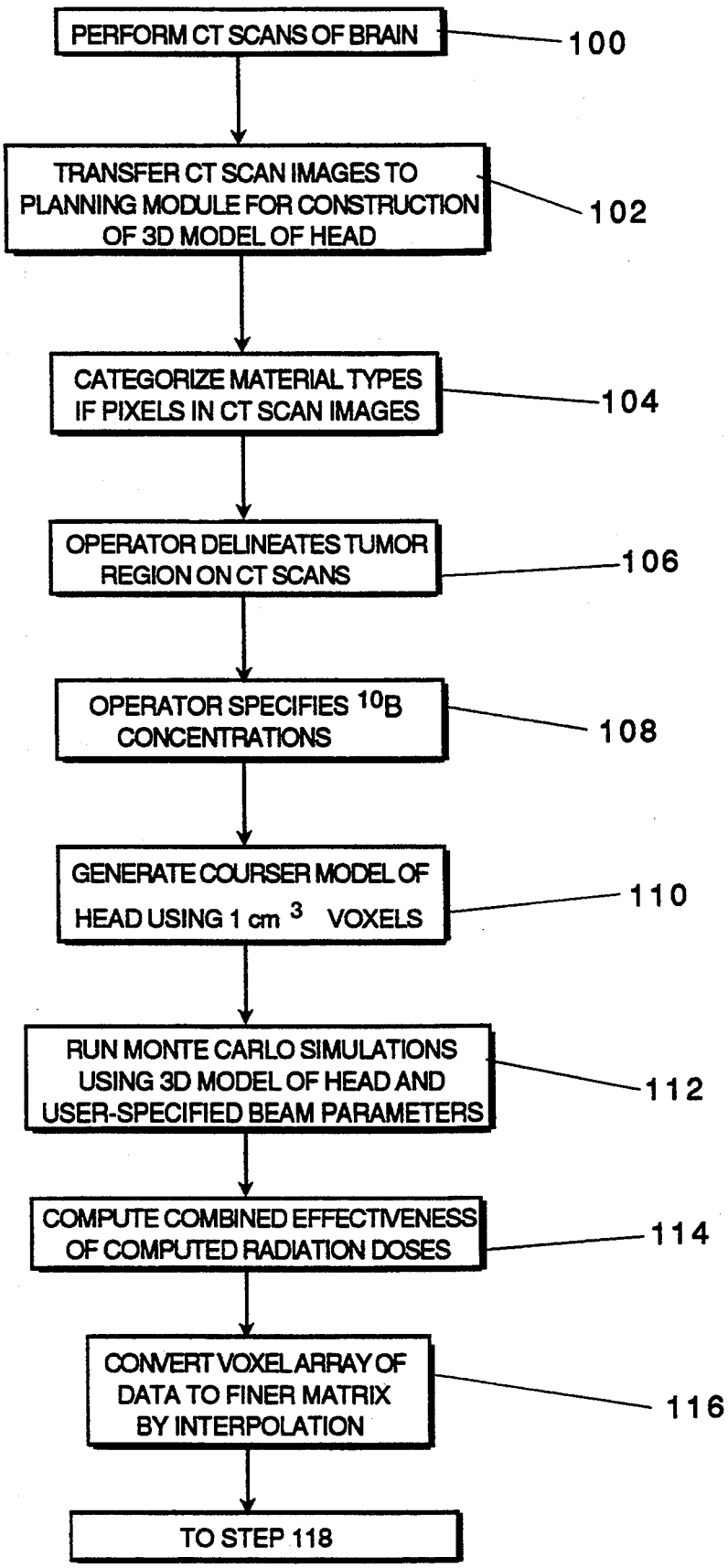
Figure 2B:
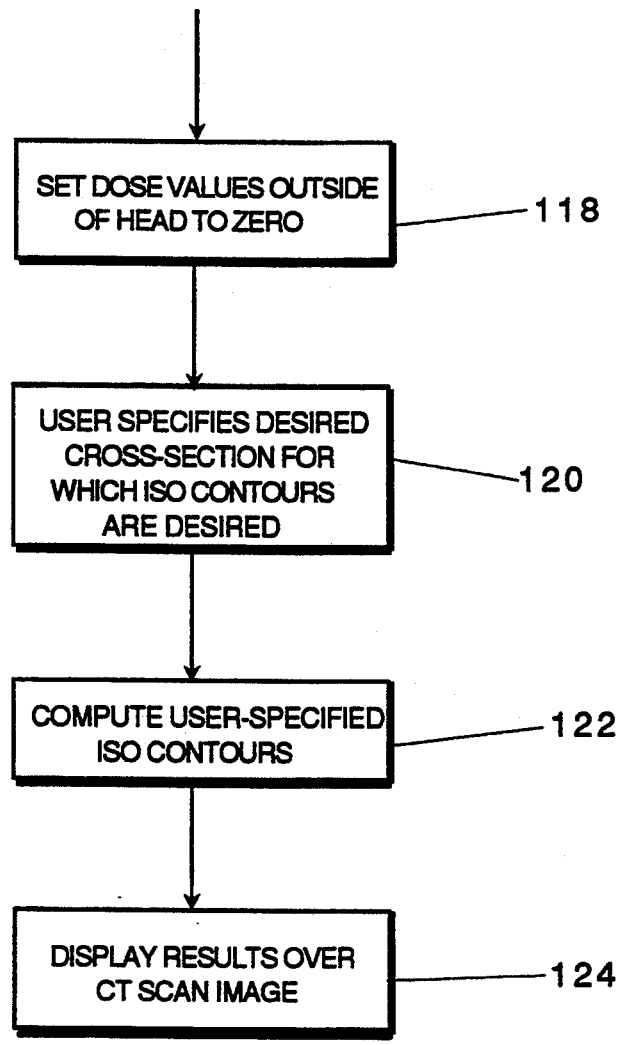
Figure 3:
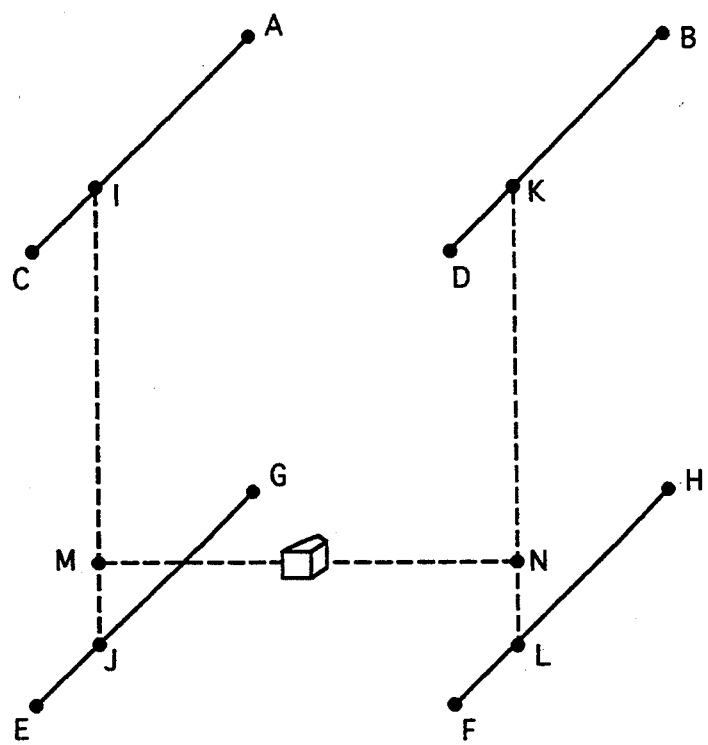

FIG. 1 is a block diagram of the neutron capture therapy planning system;

FIGS. 2A–B show the steps that are implemented using neutron capture therapy system show in FIG. 1; and FIG. 3 shows an array of voxel centers and is used to illustrate the technique for interpolating values for subvoxels.

STRUCTURE AND OPERATION

Referring to FIG. 1, a NCT treatment planning system 10 according to the invention includes a CT scanner 12 that generates a 3D image of a target organ, which in the described embodiment is a patient's head. The CT image data has a resolution of about 100 pixels per $cm^2$ per scan. An operator displays the multiple scan images on a display screen 14 one at a time and using an electronic pen device 16 on a digitizer pad that overlays display screen 14 the operator traces the boundaries of the areas which appear to contain tumor. Using the multiple CT image scans from CT scanner 12 and the pen input generated by the operator, a planning module 18 constructs a 3D model of the head, indicating its internal anatomical structures. Planning module 18 models the head as an array of 1 $cm^3$ voxels and estimates the material composition of each of the voxels.

Planning module 18 passes the 3D model of the head to a simulator 20. After the operator specifies an arrangement of one or more neutron beams, simulator 20 uses a Monte Carlo simulation technique to compute the radiation dosages throughout the head. Simulator 20 passes back to planning module 18 a set of dose matrices that specify the doses per voxel for a group of relevant radiation components.

To assist in the processing the image for display, planning module 18 uses an interpolation technique to convert the dose matrix data to a finer granularity, namely, a granularity of about 1 mm³. The operator then specifies a cross-section through the head for which the display of dosage information is desired. Using the selected cross-section of dose data and the finer granularity dose matrix data, planning module 18 computes the desired visual representation of dose information (e.g. isodose contours) and displays it on display screen 14. Planning module 18 displays the dose information as an overlay on the CT scan image showing the anatomical structure of the brain for that cross-section, thus the operator obtains an accurate one-to-one correlation between the computed dose information and the underlying anatomical structure.

The different processes implemented by the modules identified in FIG. 1 will now be described in greater detail with the aid of FIGS. 2A–B.

BUILDING THE MODEL

CT scanner 12, which in the described embodiment is a Siemens Somatome DR-3 CT scanner, generates approximately 80–130 contiguous 2 mm-thick CT scans of the patient's relevant body part (step 100). Technique factors of 125 kVp, 480 mAs, 3 second scan, orientation perpendicular to the table travel (i.e., with the gantry angle set to zero), and a hardware zoom factor of unity are used. The resulting pixels of the CT scan image have a depth resolution of about 2 mm and a transverse resolution of about 1 mm × 1 mm (actually 0.98 mm). Different protocols are used depending upon the organ of interest. In a brain tumor protocol, the scans are performed with iodinated contrast to better delineate tumor boundaries 1–2 weeks after the patient receives cytoreductive surgery for a grade III/IV astrocytoma. In a protocol for treating melanoma metastases in the proximal extremities, no contrast is used.

CT scanner 12 yields electron density information which for the present purposes closely represents the physical densities of the brain. Within a CT scan of the head, one can clearly and unambiguously differentiate air, soft tissue and bone. Moreover, it can be shown that the various soft tissues within the head (e.g. gray matter, white matter and blood) are so close in density and constituency as to be essentially neutronically equivalent. That is, they absorb and scatter neutrons in approximately the same way. Thus, in modeling the internal structure of the head, all soft tissues may be treated as the same and one can categorize the inhomogeneities in the brain as one of the three types, namely, bone, air and soft tissue.

In the described embodiment, the CT images thus acquired are transferred to magnetic tape (in 512×512×12 bit digital matrix format) which is in turn transferred to planning module 18 where it is analyzed and used to construct a 3D model of the internal structure of the head (step 102). Planning module 18 examines each pixel of every CT image and automatically assigns it one of three material types (i.e., bone, soft tissue, and air) depending upon the value of the CT data for the pixel (step 104). The material types are calculated from the CT values according to empirically derived threshold criteria to differentiate bone, soft tissue, and air as follows:

| | |
|---|---|
| < −150 H | Air |
| −150 H to + 240 H | Soft Tissue |
| > 240 H | Bone, | where H stands for Hounsfield units. A Hounsfield unit is a 0.1% change in the linear attenuation coefficient.

The physician next examines each CT scan that contains visible tumor and using the CT scanner's digital input tablet delineates tumor boundaries if possible (step 106). These boundaries are automatically transferred by planning module 18 into an extrapolated 1 cm×1 cm grid that is used to construct the Monte Carlo model.

The operator specifies the $^{10}B$ concentrations in tumor and normal soft tissue (in weight parts-per-million) that are anticipated to exist at the time of neutron irradiation (step 108). Boron accumulation in bone and air is assumed to be zero. Information concerning boron distribution is obtained from an analysis of biopsy samples following a preliminary "test" administration of the boron compound to be used shortly prior to the patient's cytoreductive surgery. The inclusion of an approximate bulk $^{10}B$ distribution in the model has previously been demonstrated to be important with respect to correcting for depression of thermal neutron flux if large fractions of the model contain more than approximately 10 ppm of $^{10}B$ at the macroscopic level (see pp. 290–291 of Ref. 1). This is also believed to be true when using P-boronophenylalanine (BPA), a boron compound that may be used to deposit boron at tumor sites within the brain.

All CT scan image pixels that fall within the tumor boundaries identified by the operator and are determined to be soft tissue are treated as tumor soft tissue having the higher boron concentration. All other pixels that are identified as soft tissue are treated as normal soft tissue with the lower boron concentration.

After planning module 18 completes its analysis of all pixels in all CT images and boron concentrations have been specified, it generates the lower resolution model of the head consisting of a 3D array of 1 cm³ cells or voxels (step 110). Each voxel in the array is made up of 500 pixels (i.e., five contiguous layers of a 10×10 CT image squares) of the original CT scan data. Planning module 18 computes the relative macroscopic volumes of bone, normal soft tissue, tumor soft tissue, and air for each voxel. To make the total number of possible cell compositions manageable (compositions are defined here as being the result of the admixtures of bone, normal soft tissue, tumor soft tissue, and air), each of the anatomical tissues and air are rounded-off to the nearest +20% fraction by volume. For example: bone, normal soft tissue, tumor soft tissue and air can each take on volume fraction values of 0%, 20%, 40%, 60%, 80%, and 100%, with the constraint that for each voxel the total percentages of the four components together add up to 100%. Given this constraint, the total number of possible combinations of the four materials is 56. Thus, any given voxel is made up of one of the 56 total possible compositions.

MODELING OF SOFT TISSUES

The element predominantly responsible for neutron transport in "soft" biological tissues is hydrogen. Its abundance (all percentage abundance values specified hereafter will be weight percent) varies from 9.6% for the lens of the eye to 11.4% for adipose tissue, although most soft tissues exhibit a smaller variability about the mean of 10.5%±0.2 (1 s.d.) (see, for example, Ref. 5). Furthermore, since soft tissues have an average physical density of 1.05 g/cm$^3$±0.02 (1 s.d.), their percent hydrogen content should be normalized to unit density to permit neutronic comparison with water, since it is the tissue's percent by weight of hydrogen per cm$^3$ that determines its radiation transport properties. The normalized average hydrogen content of soft tissues thus becomes 11.0%±0.2 (1 s.d.). Water, having a hydrogen content of 11.1% is, therefore, a very good neutronically equivalent material for virtually all soft tissues.

With regard to photon equivalence, water simulates virtually all soft tissues in the photon energy range of 100 keV to 10 MeV to within 1-2% in linear attenuation coefficient.

MODELING OF BONE

For neutron interactions, the hydrogen content of bone ranges from 3.4% (for cortical bone) to 8.5% (for spongiosa). When "bone" is identified in the CT images the corresponding pixels are assumed to be cortical bone with an adjusted hydrogen concentration of 5%, reflecting an average hydrogen content for cortical bone and spongiosa (see Ref. 6).

With regard to photon interactions, the physical densities (specific gravities) of cortical bone and spongiosa are assumed to be, respectively, 2.0 g/cm3 and 1.1 g/cm$^3$. It was calculated that the average electron density (in electrons/cm$^3$) for these two tissues is given by a material having the elemental composition of cortical bone and a physical density of 1.5 g/cm$^3$. In the present context, where photon energies are typically in the 0.5-10 MeV range, atomic number-dependent photon interactions have a very minor impact on attenuation so only electron density needs to be considered as a photon attenuation criterion.

The neutron transport errors associated with the quantized 20% increments that are used to combine the three principal tissue types and air are equivalent to splitting a 20% step from soft tissue to bone from the perspective of the corresponding change in hydrogen content. Since bone is assumed to have 5% hydrogen content and soft-tissue (represented by water) is assumed to have 11%, the quantization error is equivalent to a +0.5% error in hydrogen content and is, therefore, relatively negligible.

SPECIFYING THE NEUTRON BEAMS

In addition to marking tumor boundaries and selecting boron concentrations, the physician examines the CT images and decides what neutron beam configuration (number, direction, diameter) is desired. To specify the number and orientation of the desired neutron beams, the physician "marks" with a digitizer pen on the appropriate CT images the central-axis entrance and exit points of each desired neutron beam. Planning module 18 then calculates three unit-vectors for each neutron beam which define the geometric orientation of the beams with respect to the model.

When the materials (and $^{10}$B concentrations) in each of the 11,025 1 cm$^3$ cells have been calculated as described earlier, these data, together with the cartesian X-Y-Z coordinates of each cell, the diameters and unit vectors of each neutron beam, and the entrance and exit points of each beam as marked on the CT images are downloaded into an intermediate Monte Carlo input file. These data are, of course, reformatted as required by the Monte Carlo code. Using the CT scan generated model of the head, Monte Carlo simulations are then run (step 112).

MONTE CARLO SIMULATION

The Monte Carlo simulation code used for this work was MCNP (Monte Carlo for Neutron and Photon Transport), version 3$b$, installed on a Sun Sparc Workstation model 330. This code, originally developed for weapons research at Los Alamos Scientific Laboratory (Ref. 7), is probably the most sophisticated code of its kind from the perspective of the physics employed and its continual improvement and development by a large support staff at the Los Alamos National Laboratory.

MCNP is a coupled neutron/photon code; i.e., photon production by neutron interactions is handled during simulation by a photon production segment of the cross-section file, and does not require first generating a photon source distribution by a neutron simulation and then independently simulating the photons. The code uses pointwise continuous energy cross-section data from various sources; i.e., at the moment of any specific neutron or photon interaction, rather than "binning" the particle into a discrete energy band the actual energy of the particle determines the interpolated cross-section values that are sampled. The energy density of the cross-section data is such that interpolation between points results in less than a 1% discrepancy in reproducing the original experimental cross-section data. The cross-section data file used, ENDF/B (Evaluated Nuclear Data File available for Oak Ridge National Laboratory), includes a thermal library with corrections for chemical binding in light water for neutrons of less than 4 keV in energy, which is of critical importance when the transport medium is an aqueous one, such as in the present work.

In the described embodiment, the source beam's intensity distribution, angular distribution, and the particle energy spectrum that were used in the Monte Carlo simulations were designed to represent the epithermal neutron beam (internally designated M57) currently available at the Research Reactor at the Massachusetts Institute of Technology. The source parameters were derived by Monte Carlo simulation (also using the MCNP code) of the transport of particles from a model of the reactor core through the various functional and structural elements of the core tank, reflector, beam line structures, resonance scattering filters, etc., down to a circular 61 cm diameter plane just above the light water tank of the reactor. For all treatment planning computations this plane constituted the neutron and photon source used as the starting point of the treatment planning Monte Carlo simulations. (For further information on modeling the MIT reactor core see Refs. 8 and 9 in Table A).

To fully understand the performance of a particular neutron beam for use in NCT, it is necessary to analyze the dose not only in terms of its spatial distribution within the brain but also to disassemble it into its constituent components. This is also necessary if dose modifiers, such as Relative Biological Effectiveness (RBE) factors, are included as they are in the present case.

An "idealized" neutron beam, consisting of a current of mono-energetic epithermal neutrons incident on the model and comprising no undesirable contaminating radiation, generates four dose components that need to be examined separately, namely:

Thermal-neutron dose, principally resulting from $^{14}N(n,p)^{14}C$ thermal-neutron capture reactions, Epithermal-neutron dose, principally resulting from $^{1}H(n,n')^{1}H$ epithermal-neutron scattering reactions, Tissue induced gamma dose, principally resulting from $^{1}H(n,\gamma)^{2}H$ thermal-neutron capture reactions, and Boron-10 dose, resulting from $^{10}B(n,\alpha)^{7}Li$ thermal-neutron capture reactions.

An actual epithermal-neutron beam from a nuclear reactor, such as one of those that are currently under evaluation at the Massachusetts Institute of Technology Research Reactor, MITR-II, also include three additional dose components:

Fast-neutron dose, principally resulting from $^{1}H(n,n')^{1}H$ fast-neutron scattering reactions, but possibly including significant amounts of recoil reactions on other tissue elements, such as carbon and oxygen, Reactor core gamma dose, principally from gamma rays originating in the uranium fission process in the reactor's core (core gammas), and Neutron-induced gamma dose, resulting from gamma rays produced by the capture and inelastic scattering of neutrons by the structural materials surrounding the beam line (structure-induced gammas).

In the described embodiment, the seven dose components listed in Table I below were computed. Note that dose component number 2 is the sum of two different neutron doses, namely, epithermal-neutron dose and fast neutron dose. Component number 3 is the sum of all gamma radiations, namely, the sum of components 4, 5, and 6 (i.e., neutron-induced gammas, reactor core gammas, and tissue-induced gammas).

TABLE 1

| Dose Component | Typical Statistical Errors (%) | |
|---|---|---|
| | Shallow (1-2 cm) | Deep (7-12 cm) |
| 1. Thermal Neutrons | 4 | 5 |
| 2. Epithermal & Fast Neutrons | 12 | 15 |
| 3. Total Gammas | 30 | 22 |
| 4. Structure-Induced Gammas | * | * |
| 5. Source (Core) Gammas | * | * |
| 6. Tissue-Induced Gammas | * | * |
| 7. $^{10}B$ Dose | 4 | 5 |

Note that the errors for items 4, 5, and 6 (shown by *'s) are collectively included under item 3.

To compute the seven dose components each Monte Carlo simulation of a beam included three separate "runs" of typically 500,000 starting particles each. The three-run strategy used for separating the dose components is shown in Table 2. The numbers under the heading "Dose Components Present" identify specific dose component listed it Table 1. The multiple dose components computed in simulation type 1 are intrinsically separated by particle type (neutrons or gammas) and by particle energy.

TABLE 2

| Simulation Type | Dose Components Present | | | | | | |
|---|---|---|---|---|---|---|---|
| 1. Source Neutrons/ Tissue-Induced Gammas | 1 | 2 | * | * | * | 6 | 7 |
| 2. Source Gammas Only | * | * | * | * | 5 | * | * |
| 3. Source Neutrons/ Structure-Induced Gammas | * | * | * | 4 | * | * | * |

The first Monte Carlo simulation is performed with source neutrons only. That is, the core gammas are not used and the structure-induced gammas are set to zero. The first run yields the four dose components identified in Table 1 by 1, 2, 6, and 7. A second run includes core gammas only and no source neutrons and yields dose component number 5 of Table 1, i.e., the core gamma component. A final run includes source neutrons only (i.e., no core gammas) with the tissue-induced gammas "turned off". The final run yields component number 4 in Table 1, i.e., the structure-induced gamma radiation. From these components, the total gamma dose is computed by adding components 4, 5 and 6.

To compute absorbed dose in tissue a feature of MCNP was used which allows arbitrary nuclear reaction rates to be computed as part of the simulation (e.g. heat production by neutrons and photons). This feature allows the computation of the integral product of the neutron or photon fluence spectra at any point in the model and an energy dependent fluence-to-kerma conversion factor file ("kerma file") corresponding to each material explicitly or implicitly specified in the model.

A kerma file for water (Ref. 10) was used to compute soft tissue dose and a kerma file for 1 ppm of $^{10}B$ (Ref. 11) was used to compute $^{10}B$ dose. The latter kerma values were linearly scaled to obtain the dose for desired $^{10}B$ concentrations other than 1 ppm. For the 1 cm$^3$ cells used, absorbed dose is numerically equal to kerma for all neutron and photon energies encountered in the present simulations (Ref. 12).

As indicated earlier, Monte Carlo simulator 20 computes the doses on a per voxel basis. It is of course possible to reduce the dimensions of the cells, and hence to improve the geometric fidelity of the Monte Carlo model. To do so, however, requires a costly tradeoff in terms of computation time. Even with the existing coarse cell structure, the Monte Carlo computation time needs to be long to ensure adequate statistical accuracy of the doses computed in each cell. Table 1 shows the typical estimated statistical errors of the various dose components computed in shallow and deep regions of a head model using the 1 cm$^3$ cell structure (for single-field radiation). The total CPU time that was required to obtain these data, requiring three separate Monte Carlo simulations to compute just one beam, was about 70 hours.

The combined effectiveness of the four categories of radiation are computed as a sum of the dose components weighted by appropriate RBE's for those components (the RBE are determined relative to gamma rays) (step 114). The RBE's that used for the four categories of dose components were as follows:

TABLE 3

| Dose Component | RBE |
|---|---|
| 1. Thermal Neutrons | 2.0 |
| 2. Epithermal & Fast Neutrons | 4.0 |
| 3. Total Gammas | 0.5 |
| 7. $^{10}B$ Dose | 4.0 |

Boron-10 doses were computed implicitly, although a specified explicit bulk distribution of $^{10}B$ was included in each patient-derived model as a first-order correction for thermal neutron flux depression. For example: based on the results of surgical tissue sampling and $^{10}B$ analyses following a "test" dose of 1,BPA which will be administered to a patient scheduled to undergo NCT, tumor and normal tissue $^{10}B$ concentrations at the time of neutron irradiation might be estimated (for example) as 40 ppm and 10 ppm, respectively.

These bulk $^{10}$B concentrations are used in planning module 18 as described earlier, and allow the first-order neutron flux depression corrections to be included in the Monte Carlo simulation. If, however, based on further biopsies and $^{10}$B analyses shortly before actual neutron irradiation, it is determined that the tumor and normal tissue concentrations at the time of treatment will actually be (for example) 34 ppm and 8 ppm, respectively, the actual doses due to these latter boron concentrations can be calculated implicitly without further modification of the bulk $^{10}$B concentrations initially included in the model.

For example, if it is later determined that the ratio of boron in tumor tissue to boron in normal tissue is actually 30 ppm to 12 ppm rather than 40 ppm to 10 ppm, then the dose values that are used in planning module 18 are adjusted by simply scaling the B-10 doses. In this example, the B-10 doses for the tumor tissue are scaled up by 40/30 and the B-10 doses for normal soft tissue are scaled up 12/10.

It has been determined in previous work that at 6-9 cm depth in phantom $^{10}$B dose depression due to self-absorption is approximately 0.5%/ppm of $^{10}$B uniformly distributed within the brain (less at shallower depths) (Ref. 2). Thus, this approach to calculating $^{10}$B dose is sufficiently accurate as long as a first-order dose depression correction is made in the Monte Carlo simulation. If reasonably good first estimates are used for $^{10}$B concentrations, then it has been found that there will typically only be a 1-3 ppm error in actual amounts. Thus, the required scaling does not drastically alter results.

DISPLAY OF RESULTS

The MCNP output files resulting from the three Monte Carlo simulations (per beam) are first analyzed by a stripping program which deletes output data that are not required in the present application. What remains is a series of arrays of dose values and their associated statistical errors for each of the principal dose components itemized earlier, together with the beam geometry and orientation specifications.

The stripped output files are then transferred back to planning module 18 for further analysis and display. Planning module 18 generates one-dimensional dose profiles along any arbitrary axis, two-dimensional isodose contours in any arbitrary plane, differential dose-volume histograms, various figures-of-merit specifically designed for NCT treatment planning (see Refs. 2 and 11), and other visual displays of the dose and CT image data. One-dimensional data presentation is accompanied on the computer screen by a realistic three-dimensional icon of the body part being examined, showing the orientation of the cartesian coordinate system, the direction of the incident neutron beam(s), and the axis along which graphical data are displayed. This icon is an actual three-dimensional image of the relevant body part since it is constructed of surface contours automatically derived from the original CT images. To facilitate treatment planning, two-dimensional isodose contour displays are precisely superimposed on corresponding reformatted CT images. The images preserve the original high-resolution of the CT scans thereby maintaining visibility of small anatomical structures.

CREATION OF ISODOSE CONTOURS

To prepare the dose data for automatic isocontouring two stages of preprocessing are performed on the data. The first stage of preprocessing involves interpolating the raw dose data onto a much finer 1 mm$^3$ matrix (step 116). This is achieved by linear interpolation in three dimensions using the central values of the 1 cm$^3$ cell within which the 1 mm$^3$ voxel to be interpolated exists and the central values of the eight adjacent cells.

The interpolation technique is described with the aid of FIG. 3 which shows eight points labelled A-H representing the centers of eight neighboring 1 cm$^3$ voxels (not explicitly shown). As noted above, the output of Monte Carlo simulator 20 is a 3D matrix of dose values, one value for each voxel within the head. The dose value is assigned to center of the voxel to which it corresponds. Values for intermediate points, e.g. the center of 1 mm$^3$ subvoxel 50, are computed by interpolating between selected center points to obtain four values in an intermediate plane parallel to one of the faces of the 1 cm$^3$ cubes and containing subvoxel 50, and then interpolating between those four values to obtain a value at the location of the center of subvoxel 50. The details of the interpolation procedure, using the eight points labelled A-H are as follows.

In FIG. 3, the points I-L all lie within a plane that is parallel to the plane containing points A-B-G-H. First, linearly interpolate between points A and C, points B and D, points G and E, and points H and F to obtain values for points I, K, J and L, respectively. According to the linear interpolations, the value at point X lying between points Y and Z is equal to:

$$\text{Value}_X = \text{Value}_Y + \{(\text{Value}_Y - \text{Value}_Z) * (D_{Y-X}/D_{Y-Z})\},$$

where Value$_i$ is the value at a point i and $D_{n-m}$ is the distance between points n and m.

After obtaining the values for points I, K, J and L, find the location M of subvoxel 50 along a line connecting points I and J and also find its location N along a line connecting points K and L. Once the locations of M and N are known, linearly interpolate between the values at I and J and between the values at K and L to determine interpolated values for points M and N, respectively. With the values known for points M and N, the value for subpixel 50 can then be readily determined by using the same linear interpolation between the values at M and N.

In this manner, a value is computed for every subvoxel throughout the entire 3D space of the head model.

Cells that are outside the "skin" of cells defining the outer surface of the model contain dose values that are only virtual, since with no tissue present there is no dose despite the presence of neutron and photon fluences. If these virtual dose values were allowed to remain the isocontouring process will be greatly complicated, producing isodose contours running from inside the model into the space outside, with no opportunity for closure. To avoid this problem the second stage of data processing allows the virtual dose values to remain during the interpolation of the dose data into the 1 mm$^3$ matrix, but prior to isocontouring all virtual dose values are set to zero (step 118).

This approach is not used in the case of cells representing internal voids, since what may appear in a CT image as an internal void may in fact contain tissue (tumor or normal) for which it may be important to obtain an estimate of dose.

For similar reasons the kerma files used to convert neutron and photon fluences to doses are based on kerma values for water, even if the dose location happens to correspond to bone or a soft tissue/bone mixture. In bone it is the dose to the osteocytes and other cells that is most likely of greater clinical importance than the dose to the mineralized bone matrix per se. As in the arguments presented earlier rationalizing the similar neutron and photon transport properties of water and soft tissues, it can be shown that within the range of neutron and photon energies considered here neutron and photon kermas for water and most soft tissues (including the soft tissue components of bone mentioned above) deviate by a maximum of only about 2% (see Refs. 5 and 10).

The user then specifies the desired cross-section for display and the form in which the dose information is to be displayed (step 120). The dose information can be displayed using any of a number of different known figures-of-merit. In the described embodiment, the dose information can be displayed as a planar "advantage depth" contour (AD contour). Definitions and explanations of NCT treatment planning figures-of-merit, such as advantage depth, regional and global advantage ratio, and advantage depth dose rate are described in greater detail elsewhere (see Refs. 2 and 11, incorporated herein by reference). The simple interpretation of the AD contour is that tumor tissue within it will always receive at least as much dose as the highest dose to normal tissue anywhere else (in any plane). Thus, if the maximum dose to normal structures is designated 100%, then the contours inside the AD contour represent the corresponding doses to tumor (i.e., doses greater than 100% of the dose at the AD contour), while contours outside the AD contour correspond to doses to normal structures (i.e., less than 100% of the dose at the AD contour).

The total three-dimensional integral dose to tumor divided by that to normal structures has been previously defined as the "global advantage ratio" (GAR) (Ref. 2). The GAR may be a relevant figure-of-merit for quantifying the clinically important volume-dose response of normal brain. The various treatment parameters that can influence the GAR are described (Ref. 2).

In conventional radiation therapy the tolerance of normal brain and its vasculature depends not only on the absolute dose but also on the volume of tissue receiving that dose, or more generally, on the dose distribution. Normal structure differential and integral dose histograms can be generated by the NCT treatment planning system to aid in the clinical assessment of brain tolerance. Differential or integral dose histograms may prove to be of value in NCT treatment planning even though it is not clear that a uniform dose distribution (tumor or normal tissue) is necessarily the most optimum one.

After the user specifies the desired cross-section for display, the isocontours are plotted for that cross-section using any of a number of standard techniques known to persons skilled in the art (step 122). For example, in the described embodiment, the program which plots the isocontours computed the gradient at each point and selects a path which yields a zero gradient.

Note that the conversion of data to finer granularity creates an illusion of greater resolution than actually exists. This can be handled in any of a number of ways. For example, the person using the system can be taught to not rely on the apparent "high resolution" detail. Or the high frequency detail can be removed prior to plotting the isocontours by taking a 2D fourier transform of the data and removing the high frequency information.

Finally, the computed isocontours are displayed over the corresponding CT scan image (step 124).

TABLE A

The following is a list of the references that are referred to in the specification and are incorporated herein by reference.

1. R. G. Zamenhof, S. Clement, K. Lin, C. Lui, D. Ziegelmiller, O. K. Harling, "Monte Carlo Treatment Planning and High-Resolution Alpha-Track Autoradiography for Neutron Capture Therapy," Strahlentherapie und Onkologie, 165: 188, 1989

2. R. G. Zamenhof, S. D. Clement, O. K. Hatling, J. F. Brenner, D. E. Wazer, H. Madoc-Jones, J. C Yanch, "Monte Carlo Based Dosimetry and Treatment Planning for Neutron Capture Therapy," in: Neutron Beam Design, Development, and Performance for Neutron Capture Therapy," eds: O. K. Harling, J. A. Bernard, R. G. Zamenhof, Plenum Press, New York, 1990

3. R. G. Zamenhof, J. Brenner, J. C. Yanch, D. Wazer, H. Madoc-Jones, S. Saris, O. K. Harling, "Treatment Planning for Neutron Capture Therapy of Glioblastoma Multiforme Using an Epithermal Neutron Beam from the MITR-II Research Reactor and Monte Carlo Simulation," in: Proc. 4th Intl. Symposium on Neutron Capture Therapy, Sydney, Australia, eds: B. J. Allen, B. Harrington, Plenum Press, New York, 1991

4. F. J. Wheeler, "Improved Monte Carlo Techniques for Neutron Capture Therapy," in: Proc. of International Workshop on Macro and Microdosimetry and Treatment Planning for Neutron Capture Therapy, to be published by Harcourt Brace, Co., Philadelphia (in press)

5. I.C.R.U. Report 44, "Tissue Substitutes in Radiation Dosimetry and Measurement," International Commission on Radiation Units and Measurements, Bethesda, Md., 1989

6. M. Weissberger, R. G. Zamenhof, S. Aronow, R. M. Neet: "CT Scanning for the Measurement of Bone Mineral in the Human Spine", J. Comp. Assisted Tomog., 2:253, 1978

7. J. F. Briesmaster, ed., "MCNP—A General Monte Carlo Code for Neutron and Photon Transport, Version 3A," Los Alamos National Laboratory, LA-7396-M, Rev.2, 1986

8. E. L. Redmond II, "A Characterization of the Neutron Source in the H2O Shutter Tank of the MITR-II," Internal Report, Department of Nuclear Engineering, Massachusetts Institute of Technology, Cambridge, Mass., 1991

9. J. R. Choi, R. G. Zamenhof, J. C. Yanch, R. Rogus, O. K. Harling, "Performance of the Currently Available Epithermal Neutron Beam at the MIT Research Reactor," in: Proc. 4th Intl. Symposium on Neutron Capture Therapy, Sydney, Australia, eds: B. J. Allen, B. Harrington, Plenum Press, New York, 1991

10. R. S. Caswell, J. J. Coyne, M. L. Randolph, "Kerma Factors of Elements and Compounds for Neutron Energies Below 30 MeV," Int. J. Appl. Radiat. Isot., 33:1227, 1982

11. R G Zamenhof, B W Murray, G L Brownell, G R Wellum, and E I Tolpin: "Boron Neutron Capture Therapy for the Treatment for Cerebral Gliomas: I. An Evaluation of the Efficacy of Different Neutron Beams", Med. Phys. 2:47, 1975

12. J. R. Greening, "Fundamentals of Radiation Dosimetry," Adam Hilger, Ltd., Bristol, 1985

Other embodiments are within the following claims.

What is claimed is:

1. A method of developing a treatment plan for neutron capture therapy of a target organ containing a tumor, said method comprising:
    using a diagnostic cross-sectional scanner to scan the target organ to generate cross-sectional images of the organ;
    generating a three-dimensional model of the organ from the cross-sectional images, said model including information about variations in internal composition of the organ in addition to said tumor; and
    computing a three-dimensional array of expected radiation doses throughout the organ assuming a given arrangement of one or more neutron beams, said computing step using the three-dimensional model of the organ to compute said three-dimensional array of expected radiation doses.

2. The method of claim 1 wherein the information about variations in internal composition of the organ is represented in said model as variations in radiation transport properties in the organ.

3. The method of claim 2 wherein said diagnostic cross-sectional scanner is a CT scanner.

4. The method of claim 3 wherein the computing step uses Monte Carlo simulation techniques to compute said three-dimensional array of expected radiation doses.

5. The method of claim 4 wherein said neutron capture therapy uses boron to enhance neutron capture in selected regions of the organ, said method further comprising identifying on said image of the organ a region within the organ that is believed to contain said tumor and wherein said generating step models said region as having a higher boron concentration than the part of the organ outside said region.

6. The method of claim 4 wherein the three-dimensional model is a three-dimensional array of three-dimensional cells and wherein said model generating step further comprises assigning each of said cells a corresponding one of a plurality of predetermined materials based upon a CT image value for that cell.

7. The method of claim 6 wherein the cells are cubes of uniform dimension,

8. The method of claim 6 further comprising:
    selecting a cross-section of the organ for which dose information is desired;
    computing isocontours for the selected cross-section from the computed three dimensional array of expected radiation doses; and
    displaying the computed isocontours over a CT image of the selected cross-section.

9. The method of claim 4 further comprising:
    selecting a cross-section of the organ for which dose information is desired;
    setting the computed dose values outside of the organ to zero;
    after setting the computed dose values outside the organ to zero, computing isocontours for the selected cross-section from the three-dimensional array of expected radiation doses; and
    displaying the computing isocontours over a CT image of the selected cross-section.

10. The method of claim 4 wherein each of the cross-sectional images is a matrix of data elements, and said model generating step comprises:
    assigning one of a plurality of predetermined materials to each of said data elements of said matrices, thereby generating an intermediate model; and
    constructing the three-dimensional model from the intermediate model.

11. The method of claim 10 wherein the intermediate model is a three-dimensional array of subcells, each subcell corresponding to a different data element of the matrices of data elements, and wherein said three-dimensional model is an array of cells and wherein each cell is made up of a corresponding plurality of subcells.

12. The method of claim 11 wherein the model generating step further comprises computing for each given cell a percentage of each of said plurality of the predetermined materials that is assigned to the subcells that make up that given cell.

13. The method of claim 12 wherein the model generating step further comprises assigning to the given cell a composition that corresponds to the computed percentages of said plurality of predetermined materials that are assigned to the subcells that correspond to the given cell.

14. The method of claim 13 wherein the composition contains quantized amounts of said plurality of predetermined materials.

15. The method of claim 14 wherein the plurality of predetermined materials includes bone, soft tissue and air.

16. The method of claim 15 wherein the plurality of predetermined materials further includes tumor tissue.

17. The method of claim 16 wherein said neutron capture therapy uses boron to enhance neutron capture in selected regions of the organ, and wherein the soft tissue and the tumor are specified to contain different amounts of boron.

18. The method of claim 4 wherein the target organ is a brain.

19. A method of developing a treatment plan for boron neutron capture therapy of a patient's brain, said method comprising:
    using a diagnostic cross-sectional scanner to scan the patient's head to generate cross-sectional images of the head;
    generating a three-dimensional model of the head from the cross-sectional images, said model including information about variations in radiation transport properties inside the organ;
    computing a three-dimensional array of expected radiation doses throughout the head assuming a given arrangement of one or more neutron beams, said computing step using the three-dimensional model of the head to compute said three-dimensional array of expected radiation doses and said computing step using Monte Carlo simulation techniques to compute said three-dimensional array of expected radiation doses;
    selecting a cross-section of the patient's head for which dose information is desired;
    computing isocontours for the selected cross-section from the computed three dimensional array of expected radiation doses; and
    displaying the computed isocontours over a CT image of the selected cross-section.

* * * * *

UNITED STATES PATENT AND TRADEMARK OFFICE
CERTIFICATE OF CORRECTION

PATENT NO. : 5,341,292
DATED : August 23, 1994
INVENTOR(S) : Robert G. Zamenhof

It is certified that error appears in the above-indentified patent and that said Letters Patent is hereby corrected as shown below:

Col. 1, line 5, insert the following after "BACKGROUND OF THE INVENTION":

"The Government has rights in this invention pursuant to DOE Grant No. DE-FG02-87ER60600 awarded by the Department of Energy."

Col. 14, line 45, replace "Neet" with --Neer--.

Signed and Sealed this

Twenty-ninth Day of November, 1994

Attest:

BRUCE LEHMAN

*Attesting Officer*     *Commissioner of Patents and Trademarks*